(12) United States Patent
Hudgins et al.

(10) Patent No.: US 6,364,572 B1
(45) Date of Patent: Apr. 2, 2002

(54) AEROBIC LANDFILL BIOREACTOR

(75) Inventors: Mark P Hudgins; Bernard J Bessette, both of Aiken, SC (US); John C March, Winterville, GA (US); Scott T. McComb, Andersonville, SC (US)

(73) Assignee: American Technologies, Inc., Oak Ridge, TN (US)

( * ) Notice: Subject to any disclaimer, the term of this patent is extended or adjusted under 35 U.S.C. 154(b) by 0 days.

(21) Appl. No.: 09/432,028

(22) Filed: Oct. 29, 1999

Related U.S. Application Data

(62) Division of application No. 08/970,777, filed on Nov. 11, 1997.
(60) Provisional application No. 60/030,792, filed on Nov. 14, 1996.

(51) Int. Cl.$^7$ .................................................. B09B 1/00
(52) U.S. Cl. .......................... 405/129.35; 405/129.45; 405/129.57; 405/129.95
(58) Field of Search ................................ 210/747, 901; 588/259; 435/289.1, 290.4; 405/129.1, 129.35, 129.45, 129.57, 129.95

(56) References Cited

U.S. PATENT DOCUMENTS

| | | | | |
|---|---|---|---|---|
| 3,586,624 A | * | 6/1971 | Larson ........................ | 210/747 |
| 3,846,290 A | * | 11/1974 | Raymond .................... | 210/610 |
| 4,401,569 A | * | 8/1983 | Jhaveri et al. ............... | 210/610 |
| 4,670,148 A | * | 6/1987 | Schneider ................... | 210/603 |
| 4,765,902 A | * | 8/1988 | Ely et al. ..................... | 210/610 |
| 4,810,131 A | * | 3/1989 | Turner ......................... | 405/129 |
| 4,849,360 A | * | 7/1989 | Norris et al. ........... | 405/128 X |
| 4,867,604 A | * | 9/1989 | Bell ............................. | 405/128 |
| 5,018,576 A | * | 5/1991 | Udel et al. ................... | 166/272 |
| 5,037,551 A | * | 8/1991 | Barkley et al. ............. | 210/610 |
| 5,057,221 A | * | 10/1991 | Bryant et al. ............... | 210/610 |
| 5,111,883 A | * | 5/1992 | Savery ........................ | 166/269 |
| 5,120,160 A | * | 6/1992 | Schwengel .................. | 405/128 |
| 5,178,491 A | * | 1/1993 | Graves et al. .............. | 405/128 |
| 5,206,173 A | * | 4/1993 | Finn ............................ | 435/313 |
| 5,221,159 A | * | 6/1993 | Billings et al. ............. | 405/128 |
| 5,228,804 A | * | 7/1993 | Balch ......................... | 405/128 |
| 5,265,979 A | * | 11/1993 | Hansen ....................... | 405/129 |
| 5,277,518 A | * | 1/1994 | Billings et al. ............. | 405/128 |
| 5,279,740 A | * | 1/1994 | Basile et al. ................ | 210/610 |
| 5,286,140 A | * | 2/1994 | Mather ....................... | 405/128 |
| 5,324,138 A | * | 6/1994 | Hansen ....................... | 405/129 |
| 5,362,181 A | * | 11/1994 | DenBesten .................. | 405/129 |
| 5,375,944 A | * | 12/1994 | Kotani et al. ............... | 405/129 |
| 5,384,048 A | * | 1/1995 | Hazen et al. ............... | 210/605 |
| 5,417,736 A | * | 5/1995 | Meyer ............................. | 71/9 |
| 5,481,815 A | * | 1/1996 | Murphy et al. ............... | 37/344 |
| 5,525,008 A | * | 6/1996 | Wilson ........................ | 405/128 |
| 5,564,862 A | * | 10/1996 | Markels et al. ............. | 405/129 |
| 5,570,973 A | * | 11/1996 | Hunt ........................... | 405/128 |
| 5,605,417 A | * | 2/1997 | Englert et al. .............. | 405/129 |

* cited by examiner

*Primary Examiner*—David A. Redding
(74) *Attorney, Agent, or Firm*—Michael A. Mann; Nexsen Pruet Jacobs & Pollard, LLC

(57) ABSTRACT

The present invention includes a system of decomposing municipal solid waste (MSW) within a landfill by converting the landfill to aerobic degradation in the following manner: (1) injecting air via the landfill leachate collection system (2) injecting air via vertical air injection wells installed within the waste mass; (3) applying leachate to the waste mass using a pressurized drip irrigation system; (4) allowing landfill gases to vent; and (5) adjusting air injection and recirculated leachate to achieve a 40% to 60% moisture level and a temperature between 120° F. and 140° F. in steady state.

18 Claims, 1 Drawing Sheet

AEROBIC LANDFILL BIOREACTOR

1. PRIORITY CLAIM

This application is a divisional of U.S. application Ser. No. 08/970,777 filed on Nov. 11, 1997, which claims the benefit of U.S. Provisional Application No. 60/030,792 filed on Nov. 14, 1996.

The U.S. Government may have rights in the present invention based on the funding of a demonstration project through Cooperative Agreement Number DE-FC09-95SR18525 between the U.S. Department of Energy Savannah River Operations Office and the Southeastern Technology Center.

2. FIELD OF THE INVENTION

The present invention relates to landfill operation and to bioreactors. In particular, the present invention relates to an aerobically operated landfill. The present application claims the benefit of the priority date of provisional application serial No. 60/030,792, filed Nov. 14, 1996.

3. BACKGROUND OF THE INVENTION

Aerobic decomposition of wastes is well known. Composting, for example, has been practiced in agriculture for centuries. However, most modern landfills are operated in an aerobic manner because of regulatory requirements. Nonetheless, there are advantages to aerobic decomposition of the types of wastes that are found in landfills and, accordingly, considerable investigation and interest exists in this art.

For example, in lysimeter tests conducted by the University of South Florida, it was shown that degradation of municipal solid wastes (MSW) can be enhanced by the application of water, the recycling of leachate, and the addition of air. Employing these processes on shredded MSW in a vertical lysimeter, waste settlement rates of greater than 25% were observed within 60 days. In addition, these tests showed significant improvement in leachate quality based on biochemical oxygen demand (BOD) and volatile solids. In light of this work and other MSW treatment studies, it is estimated that landfills that have at least a 50% organic fraction of waste, could achieve a MSW settlement of a least 15% by volume.

Although there are advantages to aerobic decomposition of wastes and keen interest in this art, methods for the demonstrated safe operation of landfills in an aerobic manner or for the cost-effective conversion of landfills from anaerobic to aerobic operation are not known prior to the present invention.

SUMMARY OF THE INVENTION

The present invention, briefly described, is an improved aerobic landfill, perhaps by converting an anaerobic landfill. The present invention increases the rate of waste stabilization, decreases the rate of production of methane gas, reduces the levels of toxic organics, and decreases the volume of leachate. As a result, the present invention presents a significantly reduced threat to the environment and a significant reduction in the cost associated with operation, closure, and post-closure of the landfill. The effectiveness of the aerobic landfill is based on applying the correct balance of air and recirculated leachate to the waste in the landfill. The recirculation of leachate provides, not only an ample supply of moisture, but sufficient oxygen, food and nutrients for organisms in the waste mass. Additional nutrients, such as those from sewer sludge or nitrogen, are not necessarily required for this process to operate.

The present invention also uses a combination of air injection through vertical wells inserted into the waste mass and horizontal leachate collection system piping. This combination allows flexibility in the application of air and leachate to the proper proportions to achieve a safe waste mass temperature preferably between approximately 120° F. and approximately 140° F. and most preferably close to 135° F. Maintaining temperatures below 150° F. is essential to preclude killing the microorganisms needed for the landfill to operate aerobically.

The present invention includes a unique system of degrading municipal solid waste (MSW) within a landfill by converting an existing anaerobic landfill to aerobic degradation in the following manner: (1) use of the landfill leachate collection system to inject air (2) vertical air injection wells installed within the waste mass; (3) a pressurized drip irrigation system for dripping leachate; (4) landfill gas vents; and (5) control systems for balancing air injection and recirculated leachate.

The primary goals of this invention are to stabilize waste and to reduce landfill operating costs and liabilities. After the waste is stabilized and rendered harmless, the landfill may be covered and redeveloped for other uses, or re-used.

Aerobically decomposing the waste in-place stabilizes the waste mass more quickly, reduces toxic organics in the leachate, reduces methane gas production, and decreases the volume occupied by the waste. Aerobic decomposition of the waste is accomplished by an engineered system referred to as an "aerobic landfill bioreactor" or ALB. The ALB achieves optimal aerobic degradation of organic matter at safe waste mass temperatures and minimizes exposure of leachate or waste mass to human health and the environment. The present invention is confirmed by data collected during actual field applications performed by the inventors. An aerobic landfill bioreactor (ALB) system was installed and operated by the inventors at an active landfill in Grovetown, Georgia. This ALB system demonstrated over a nine month period that municipal sanitary landfills can cost-effectively be converted from anaerobic to aerobic degradation processes. It was proven through actual experience that the injection of air into the waste mass combined with the recirculation of leachate aerobically degrades MSW while waste mass temperatures remain stable between 120 degrees F. and 140 degrees F. This process, in turn, increases the rate of waste stabilization, decreases the production of methane, reduces the level of toxic organics, and decreases the production of leachate.

Those familiar with landfill operation will understand from a careful reading of the Detailed Description of Preferred Embodiments that many other features and advantages are in the present invention.

DETAILED DESCRIPTION OF THE INVENTION

Figure 1:
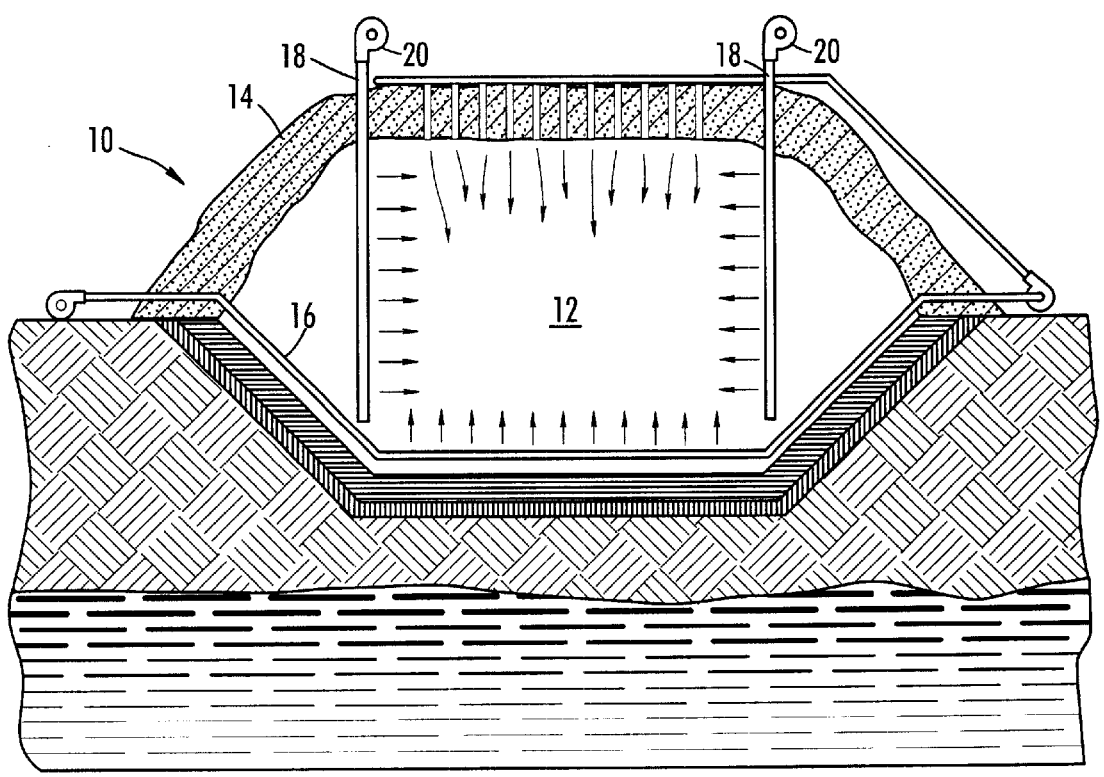
FIG. 1 is schematic section view of a landfill according to a preferred embodiment of the present invention.

Current regulatory requirements for sanitary landfills (Subtitle D of the Resource Conservation and Recovery Act) require that landfills be lined and include leachate collection systems to prevent leachate movement into the subsurface environment. In addition, landfills are required to have an impermeable cap to prevent infiltration of rainwater into the waste mass, thus minimizing the production of leachate. Although these requirements have been established in an effort to protect human health and the environment, this system of solid waste disposal creates a "dry-tomb" environment within the landfill. In turn, this environment inhibits the infiltration of oxygenated water and air into the waste mass. As a result, microbes in the landfill consume the little available oxygen, and the waste mass will degrade only very slowly under anaerobic conditions.

Anaerobic conditions have several negative effects including the prolonged existence of an unstablized waste mass, increased metals dissolution into the landfill leachate, the formation of toxic daughter compounds in the leachate such as vinyl chloride, and the production of methane, a "green house gas" as considered by EPA regulations. According to the EPA, "liner and leachate collection ultimately fail due to natural decomposition . . . " (EPA, 1988). In 40 CFR 258, EPA recognizes that "Once the unit is closed, the bottom layer of the landfill will deteriorate over time and consequently, will not prevent leachate transport out of the unit." Therefore, this system of solid waste disposal increases the potential for toxic constituents in the landfill leachate to reach local groundwater and prolongs the requirement for methane management. The net effects include long-term landfill liabilities, increased landfill operational costs and landfill closure costs as well as long-term post-closure monitoring and maintenance costs. As a result of the problems associated with anaerobic degradation, extensive closure and monitoring regulations have been promulgated by the federal government and the states. Furthermore, the system dictated by current regulations does not solve the issue of ultimate MSW disposal since future MSW management could still be required beyond the landfill's planned post-closure period.

Active aerobic biodegradation processes, such as municipal waste composting, have demonstrated for years that the biodegradable mass of MSW can be stabilized in a significantly shorter time than that required under anaerobic conditions by adding air and moisture to the waste mass. In addition, recirculating landfill leachate through the waste mass continually re-introduces indigenous, facultative microorganisms and nutrients to the carbon sources, while providing a good supply of moisture.

Safe, aerobic biodegradation of MSW is achieved in-situ using the present invention whereby the landfill itself serves a large bioreactor. By maintaining an aerobic environment, indigenous, facultative bacteria consume oxygen and covert the biodegradable mass of MSW to mostly carbon dioxide and water, with a stabilized humus remaining. This invention decreases the levels of methane gas in the landfill as well as the concentrations of organic compounds in the waste mass and leachate, thereby reducing the need for methane gas management and leachate treatment since the landfill itself becomes an active treatment bed. The increase in the rate of waste degradation results in an increase in the rate of waste subsidence (settlement). This creation of landfill "air space" results in an extension of the useful life of the facility.

The present invention reduces the cost associated with compaction of the waste. Typically, landfill waste mass compaction is performed at one-foot incremental depths to compact the most waste into a given volume. The invention enables better distribution of air and water throughout the entirety of the waste mass for more complete decomposition in minimum time because less compaction of the waste benefits the operator. Furthermore, compaction with the invention should be done so that the density of the waste when compacted is less than the usual 1,300 lbs per cubic yard so that air and water flow through the waste mass is satisfactory but the mass remains physically stable.

To demonstrate this invention, and aerobic landfill bioreactor (ALB) system was installed and operated by the inventors within the active 8-acre "Subtitle D" portion of the Columbia County Baker Place Road Landfill (CCBPRL) in Grovetown, Ga. (USA). Since January 1997, the ALB system has demonstrated that this Subtitle D municipal sanitary landfill can cost-effectively be converted from anaerobic to aerobic degradation processes, and that the MSW can be aerobically degraded by injecting air into the waste via vertical air injection wells and the existing leachate. The primary goals of this invention are to stabilize MSW and to reduce landfill operation costs and liabilities. After the waste is stabilized and rendered harmless, the landfill is compacted, covered and redeveloped for other uses. Alternatively, the composted (humus) product may be removed, screened for further removal of the recyclable products and may be re-used as temporary soil cover and the landfill reused.

As illustrated in FIG. 1, this invention includes the use of the landfill's leachate collection system for distribution of air into the waste mass. FIG. 1 illustrates a landfill according to a preferred embodiment of the present invention. Landfill 10 contains a waste mass 12 with a cap 14 thereover. At the bottom of waste mass 12 is a leachate collection system 16 that is used for collecting leachate and for injecting air into waste mass 12 from the bottom. Augmenting air injection via leachate collection system 16 are a pair of vertical wells 18 connected to blowers 20.

The leachate from leachate collection system 16 is recirculated through waste mass 12 by dripping it through cap 14 as will be described in more detail below.

In cases where the leachate collection system consists of PVC piping imbedded in a permeable gravel drainage layer, this gravel layer and piping serves as a plenum for the landfill, and thus an effective conduit for airflow into the waste mass. The use of vertical air injection lines augments the air from the leachate collection piping and helps to balance air distribution throughout the waste mass. In addition, landfill leachate is recirculated throughout all portions of a landfill using a pressurized drip irrigation system.

The results of the CCBPRL ALB show: 1) a significant increase in the biodegradation rate of the MSW over anaerobic process, 2) reduction in the volume of leachate as well as the metal and organic concentrations in leachate, and 3) significantly reduced methane generation, all while maintaining an optimum moisture content of the waste mass and stabilized waste mass temperatures.

Overall, the CCBPRL ALB system performed extremely well. The analyses of vapor samples, leachate chemistry and biological activity confirm that the waste mass degrades aerobically. In addition, the strength of the waste mass was reduced.

The landfill's air injection system is preferably comprised of electric blowers fitted with air filters that are connected to the existing leachate collection system cleanout ports, which are typically located along the sides of a landfill. Areas that required more air as the system operates are augmented by additional blowers connected to PVC piping and supplied through the vertical air injection. The air duct piping is typically corrugated plastic pipe. Vertical air wells are made of PVC pipe set at appropriate intervals throughout the waste.

Air and leachate are supplied to the waste in a controlled manner to optimize aerobic conditions. The air and leachate distribution systems are designed to be flexible to accommodate the types and variability of the landfill waste. As a result, the embodiment of the invention will differ from landfill to landfill as to the spacing of the air and leachate recirculation lines, monitoring points, and any required nutrient addition.

The present landfill's leachate recirculation system includes injection of leachate through an intermediate clay cap or cover. Leachate that has been collected in the landfill's holding tank, pond, or other collection system is pumped via the leachate recirculation system into the waste mass via drip emitters which includes small diameter hoses installed through holes formed in the intermediate cover and enters the top of the waste. These holes are backfilled with sand and clay after the hoses of the drip emitters are deployed. The leachate then percolates downward from the emitters through the waste mass. The quantity of leachate supplied is sufficient to keep the waste mass moist, roughly 40% to 60% by weight, although the leachate is initially added to saturate the waste mass. Excess leachate and percolated leachate that is not consumed by the aerobic process is captured by the leachate collection system and returned to the leachate tank or pond.

The landfill's leachate recirculation and air injection systems are balanced by adjusting leachate and air delivery into the waste mass to achieve optimum moisture content and temperatures. Improper balancing of air and leachate can lead to elevated waste mass temperatures. If temperatures of the waste mass begin to increase, leachate application should be increased. If temperatures decrease, oxygen levels should be increased by increasing air flow. Additionally, if oxygen levels begin to decline, air flow should be increased to maintain the rate of oxygen consumption. Increase air flow can cause the cooling of the waste mass and require the proper balance be determined in the field.

Upon completion of ALB operation on a section of waste, the leachate recirculation system can be easily removed and placed on top of a new section or "lift" of waste, minimizing material cost. A schematic of a typical ALB is shown in FIG. 1.

Leachate is applied to the waste via a pressurized PVC piping and flexible hose system installed atop an intermediate cover which overlies the waste. In an existing anaerobic landfill that is being converted according to the present system to an aerobic landfill, the intermediate soil covering must first be removed or provisions made to direct the air and leachate into the waste mass. Removal of the soil cover is essential to preclude the formation of barrier layers that will restrict air and water flows within the waste mass, so long as the physical stability of the waste is not compromised.

As leachate is pumped to this system, it enters the PVC header piping and then is transferred to a series of lateral hoses that have pressure-rated drip emitters installed at equal intervals. The emitters include small diameter rubber tubing that extend down through the clay cap through holes formed in the cap and that are then backfilled with sand and clay when the array of emitters is deployed over the site. The leachate flows through these emitters into the waste mass at a constant rate. Ultimately the leachate is applied to the waste where it percolates evenly and downward throughout the waste. The flow rate of leachate is adjusted by either changing the type of emitter, the use of gate valves, or selectively closing off or adding leachate hoses, tubing, or PVC piping.

Air is applied to the waste via the landfill's leachate collection system which underlies the waste mass and through vertical air injection wells that are installed from above the waste. Blowers are connected to each of the leachate collection system cleanout ports that are connected to system piping. As air is forced into the ports, the leachate collection system is pressurized so that the air travels through the leachate collection system piping, and then evenly and outwardly through the piping slotting (or screened casing) and upward through the waste mass. If the quantity of air reaching the waste is insufficient, air is applied to these areas using vertical air injections wells. In these cases, PVC wells with slotted casing, or screens, are installed vertically into the waste mass and connected together via a common air header system (piping) that is installed atop the intermediate landfill cover. Blowers are connected to the air header system to provide air to the vertical wells. The wells are installed into waste to provide the appropriate ratio of oxygen to moisture. The air flow rate is adjusted by either adding/deleting air wells, selectively isolating wells through valving, or shutting off blowers to selected areas.

Data collection is vital for optimizing the performance of the landfill and to ensure its safe and efficient operation. Waste mass moisture content, temperature and off-gas concentrations (volatile organic compounds, carbon dioxide, oxygen, and methane) are measured using vapor points and temperature probes that are installed directly into the waste. Leachate analyses over the course of the operation include, at a minimum, acidity, total kjeldahl nitrogen (TKN), biochemical oxygen demand (BOD), chemical oxygen demand (COD), metals, and volatile organic compounds (VOC). Although monitoring is important and a number of parameters must be monitored, the actual monitoring can be automated so that it requires only minimal time for the landfill operator. Adjustments to the system are made based on this data. Automation of system components such as air and leachate systems also minimizes the time requirements needed from landfill operators. The rate of landfill stabilization, or point at which the environmental risk of to the public is minimized, can be defined in terms of rates of decreased concentrations of leachate toxics and maximized waste mass subsidence. Typically, in nine months, a substantial quantity of waste mass can be stabilized.

Using the present invention, oxygen levels increase in much of the waste mass within a short time after air injection begins, but begins to drop again, typically about 14 days after commencement of the operation. In conjunction with this increase, the carbon dioxide concentration initially drops and then rises in close correlation with the changes in oxygen concentrations. Shortly, methane production decreases. When taken together with measured methane levels, oxygen and carbon dioxide readings indicate a transformation from anaerobic to at least partially aerobic metabolism: carbon dioxide rises as oxygen is consumed and methane production falls off. The invention therefore provides for direct measurements of the waste degradation using vapor points, moisture probes, and thermocouples inserted in the waste. The landfill's aerobic operation is optimized by adjusting air injection and leachate application rates so that the waste mass temperatures remain stable preferably between approximately 120 degrees F. and approximately 140 degrees F. after aerobic conditions have been reached and most preferably between approximately 130° F. and approximately 135° F. Waste mass temperatures above 150 degrees F. increase the potential for landfill fires and killing off the effective respiring organisms. Target waste mass moisture is roughly 40%–60% by weight following the initial saturation of the waste mass. Moisture can be estimated by taking samples of waste and analyzing them and averaging the results or by measuring a related parameter such as electrical resistivity of a gypsum block placed in the soil.

Odor is less of a nuisance as a result of the reduced concentration of noxious gasses. Additional odor control is obtained by the use of a biofilter material added to a semi-permeable, temporary surface cover.

Landfill subsidence is monitored by physical survey or geophysical monitoring devices. The biodegradation rate of the waste mass is estimated by using carbon dioxide and methane production rates, oxygen consumption, and waste mass temperatures.

Aerobic landfill operation according to the present invention also improves leachate quality, and especially the levels of Biochemical Oxygen Demand (BOD) and concentrations of Volatile Organic Compounds (VOC) in the leachate. The landfill showed reductions in BOD and VOCs. BOD was reduced by at least 70%, as were organics such as methyl-ethyl ketone (MEK).

The invention also reduces the volume of leachate generated by the landfill. This is caused by the evaporative effects of the higher waste mass temperatures coupled with the field capacity of the waste mass to absorb moisture.

It will be apparent to those skilled in the art of aerobic landfill operation that many changes and substitutions can be made to the preferred embodiments described above without departing from the spirit and scope of the invention, defined by the appended claims.

What is claimed is:

1. A system for decomposing a waste mass, said system comprising:
    a landfill containing a waste mass
    a leachate recirculation system having
        means for collecting leachate from said waste mass,
        means for storing collected leachate, and
        means for dripping collected leachate into said waste mass;
    an air injection system having
        first means for injecting air into said waste mass, said first injecting means injecting air through said leachate collection means up through said waste mass, and
        second means for injecting air into said waste mass, said second injecting means injecting air from the top of said waste mass; and
    a control system for regulating said leachate recirculation system and said air injection system so that temperature of said waste mass is maintained below approximately 140° F. and said waste decomposes aerobically.

2. The system as recited in claim 1, wherein said control system maintains the moisture content of said waste mass at roughly 40% 60% by weight.

3. The system as recited in claim 1, wherein said second air injecting means further comprises plural vertical wells bored into said waste mass.

4. The system as recited in claim 1, wherein said control system further comprises means for monitoring said leachate for acidity, TKN, BOD, COD, metals, and VOCs.

5. The system as recited in claim 1, wherein said leachate collection means further comprises leachate cleanout ports, and wherein said first air injection means further comprises:
    air filters; and
    blowers, said blowers blowing air through said filters and into said leachate cleanout ports.

6. The system as recited in claim 1, wherein said control system maintains the temperature of said waste mass at not less than approximately 120° F.

7. A system for decomposing a waste mass, said system comprising:
    a landfill containing a waste mass
    a leachate recirculation system having
        means for collecting leachate from said waste mass,
        means for storing collected leachate, and
        means for dripping collected leachate into said waste mass;
    an air injection system having
        first means for injecting air into said waste mass, said first injecting means injecting air up through said leachate collecting means; and
        second means for injecting air into said waste mass, said second injecting means injecting air from the top of said waste mass; and
    a control system for regulating said leachate recirculation system and said air injection system so that temperature of said waste mass is maintained below approximately 140° F. and said waste decomposes aerobically.

8. The system as recited in claim 7, wherein said control system maintains the moisture content of said waste mass at roughly 40% to 60% by weight.

9. The system as recited in claim 7, wherein said second air injecting means further comprises plural vertical wells bored into said waste mass.

10. The system as recited in claim 7, wherein said control system further comprises means for monitoring said leachate for acidity, TKN, BOD, COD, metals, and VOCs.

11. The system as recited in claim 7, wherein said leachate collection means further comprises leachate cleanout ports, and wherein said first air injection means further comprises:
    air filters; and
    blowers, said blowers blowing air through said filters and into said leachate cleanout ports.

12. The system as recited in claim 7, wherein said control system maintains the temperature of said waste mass at not less than approximately 120° F.

13. The system as recited in claim 12, wherein said control system further comprises means for monitoring said leachate for acidity, TKN, BOD, COD, metals, and VOCs.

14. A system for decomposing a waste mass, said system comprising:
    a landfill containing a waste mass
    a leachate recirculation system having
        means for collecting leachate from said waste mass,
        means for storing collected leachate, and
        means for dripping collected leachate into said waste mass;
    an air injection system having
        first means for injecting air into said waste mass, said first injecting means injecting air through said leachate collection means up through said waste mass, and
        second means for injecting air into said waste mass, said second injecting means injecting air from the top of said waste mass; and
    a control system for regulating said leachate recirculation system and said air injection system so that temperature of said waste mass is maintained below approximately 140° F. and said waste decomposes aerobically, said control system maintaining the moisture content of said waste mass at roughly 40% to 60% by weight.

15. The system as recited in claim 14, wherein said second air injecting means further comprises plural vertical wells bored into said waste mass.

16. The system as recited in claim 14, wherein said control system further comprises means for monitoring said leachate for acidity, TKN, BOD, COD, metals, and VOCs.

17. The system as recited in claim 14, wherein said leachate collection means further comprises leachate cleanout ports, and wherein said first air injection means further comprises:

air filters; and blowers, said blowers blowing air through said filters and into said leachate cleanout ports.

18. The system as recited in claim 14, wherein said control system maintains the temperature of said waste mass at not less than approximately 120° F.

* * * * *